United States Patent [19]

Seidehamel et al.

[11] 3,985,897

[45] Oct. 12, 1976

[54] OCULAR HYPOTENSIVE PROCESS EMPLOYING DEXTROROTATORY SULFONAMIDOPHENETHANOLAMINES

[75] Inventors: Richard J. Seidehamel; Kendrick W. Dungan, both of Evansville, India

[73] Assignee: Mead Johnson & Company, Evansville, Ind.

[22] Filed: Nov. 14, 1974

[21] Appl. No.: 523,937

Related U.S. Application Data

[60] Division of Ser. No. 427,274, Dec. 21, 1973, Pat. No. 3,885,047, which is a continuation-in-part of Ser. No. 263,496, June 16, 1972, abandoned.

[52] U.S. Cl. .................................................. 424/321
[51] Int. Cl.² ........................................... A61K 31/18
[58] Field of Search ...................................... 424/321

[56] References Cited

UNITED STATES PATENTS

| | | | |
|---|---|---|---|
| 3,618,604 | 11/1971 | Ness.................................. | 128/260 |
| 3,660,487 | 5/1972 | Larsen et al. .................. | 260/556 A |

OTHER PUBLICATIONS

*New Drugs*, 1966 Ed., pp. 327–330.

*Chem. Abstr.* vol. 65, (1966) 2837; vol. 71 (1969) 59474b; vol. 74 (1971), 123505d.

*Primary Examiner*—Frederick E. Waddell
*Attorney, Agent, or Firm*—R. H. Uloth; R. E. Carnahan

[57] ABSTRACT

Dextrorotatory stereoisomers of beta-adrenergic stimulatory phenethanolamines such as isoproterenol, soterenol, salbutamol, carbuterol, terbutaline, and metaproterenol lower normal or elevated intraocular pressure when topically administered to the eye. Reduction in intraocular pressure is of particular importance in the treatment of glaucoma, a disease marked by ocular hypertension. The dextrorotatory phenethanolamine compounds employed in the process of the present invention are notable for the low order of adrenergic activity in contrast to levorotatory and racemic stereoisomeric forms which are very potent beta-adrenergic stimulatory agents. Consequently, those side effects generally associated with adrenergic activation such as tachycardia, mydriasis, hypertension and hypotension are absent.

7 Claims, No Drawings

OCULAR HYPOTENSIVE PROCESS EMPLOYING DEXTROROTATORY SULFONAMIDOPHENETHANOLAMINES

CROSS-REFERENCE TO RELATED APPLICATION

This application is a divisional application of U.S. patent application Ser. No. 427,274 filed Dec. 21, 1973 and now U.S. Pat. No. 3,885,047, which is a continuation-in-part application of U.S. patent application Ser. No. 263,496, filed June 16, 1972, and now abandoned.

FIELD OF THE INVENTION

This invention involves a process and compositions of the drug, bio-affecting, and body treating type. Topical treatment of the eye with a solution of d-phenethanolamines such as d-isoproterenol, d-soterenol, d-salbutamol, d-carbuterol, d-terbutaline, d-metaproterenol and the like or a salt thereof is involved.

DESCRIPTION OF THE PRIOR ART

Glaucoma is a disease of the eye characterized by a progressive increase in intraocular pressure which occurs over a prolonged period of time which if untreated continues until the optic nerve is damaged and blindness results. The goal in the treatment of glaucoma is to reduce the intraocular pressure sufficiently to prevent damage to the optic nerve. The adrenergic amine epinephrine applied topically to the eye is a widely used treatment. Miotics which include certain parasympathomimetics such as pilocarpine and cholinesterase inhibitors such as physostigmine are also widely used topically. Improved drugs for topical application to the eye to reduce intraocular pressure are needed, however, due to side effects caused by existing drugs. Common undesired effects induced by the miotics include twitching of the eye lids, browache, headache, ocular pain, conjunctival congestion, etc. Localized allergy occasionally develops. Absorption of the topically applied drug occasionally causes systemic effects. This is particularly true with the cholinesterase inhibitors which may cause salivation, sweating, nausea, vomiting, bradycardia, hypotension, etc., and with epinephrine which may cause tachycardia, hypertension, headaches, sweating, tremors, etc. The alpha-adrenergic stimulating action of epinephrine frequently causes mydriasis and sometimes retinal maculopathy on prolonged usage. Epinephrine is contraindicated in many instances.

Isoproterenol, whose adrenergic action differs from epinephrine in that it is considered almost exclusively a beta-adrenergic stimulator, has been evaluated by Ross and Drance, Arch. Ophthal., 83, 39–43 (1970), in patients with ocular hypertension. Satisfactory reduction in intraocular pressure as a result of ocular instillation of a 5% isoproterenol hydrochloride solution was obtained but, concomitant side effects of a serious nature were also seen which prohibited the practical use of isoproterenol for glaucoma treatment. Among side effects associated with the administration of isoproterenol for reduction of intraocular pressure were marked and dangerous tachycardia of up to 100 to 150 beats per minute as well as palpitations, a nervous feeling, and weakness.

Salbutamol, another relatively pure beta-receptor stimulant, has also been tested for effects on intraocular pressure. According to G. D. Patterson and G. Patterson, Postgraduate Medical Journal, 122–124 (1971), ocular instillation of 4% salbutamol in glaucomatous patients lowered intraocular pressure. However, the treatment was not satisfactory in that a considerable proportion of patients receiving salbutamol developed side effects such as a hyperaemic condition of the conjunctiva with an associated irritation of the eyelid as well as a tachyphylactic change in potency of salbutamol therapy. In regard to potency, these investigators established that a concentration of 4% salbutamol (racemate) induced a fall in intraocular pressure equivalent to 1% (levorotatory) adrenalin and stated that the equivalency ratio of levorotatory adrenalin to levorotatory salbutamol would be of the order of 2:1 rather than the apparent 4:1 inasmuch as the levorotatory stereoisomer of salbutamol was considered to be the active component in dl-salbutamol. Patterson and Patterson (supra) base this conclusion regarding activity of d-salbutamol and l-salbutamol compared to the racemate on the fact that, like the stereoisomers of isoproterenol, the dextrorotatory stereoisomer of salbutamol is essentially inactive with only about 0.02 the activity of the levorotatory stereoisomer as a beta-adrenergic stimulant.

SUMMARY OF THE INVENTION

This invention relates to a process for lowering intraocular pressure. More particularly, the present invention is concerned with the process of lowering intraocular pressure in the mammalian eye which comprises topical application thereto an effective ophthalmologically acceptable amount of the dextrorotatory stereoisomer of compounds and ophthalmologically acceptable acid addition salts thereof selected from the group consisting of a compound of Formula I

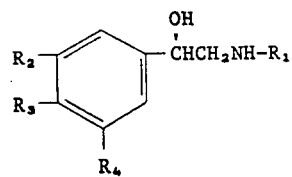

Formula I wherein $R_1$ is isopropyl or tert.-butyl; $R_2$ is hydroxy, hydroxymethyl, ureido or methanesulfonamido; and one of $R_3$ and $R_4$ is hydrogen and the other is hydroxy.

The terms "hydroxymethyl", "ureido", and "methanesulfonamido" used herein refer to the radicals $HOCH_2-$,

and $CH_3SO_2NH-$ respectively.

The term "ophthalmologically acceptable acid addition salts" used herein in describing the salts of the phenethanolamines characterized by Formula I, is intended to define those salts and compositions which are non-toxic or non-irritating on topical application to the eye, storage stable, and otherwise generally in accord with the requirements, practicalities and good pharmaceutical practice with respect to ophthalmic products. By way of example there can be mentioned those salts derived from organic and inorganic acids which are not irritating to the eye such as hydrochloric, hydrobromic, sulfuric, phosphoric, methanesulfonic, acetic, citric, malic, succinic, lactic, tartaric, benzoic, and the like.

It is to be understood that the symbols "$d$, $l$, and $dl$" employed herein are used in accord with standard chemical nomenclature and refer to dextrorotatory, levorotatory and racemic stereoisomeric forms, respectively.

Prior attempts to use isoproterenol for reducing intraocular pressure on topical application to the eye utilized the racemate (Ross and Drance, supra) or the pure levorotatory form (McDonald, et al., Archives of Ophthalmology, 82, 381–384 (1969)) because the intraocular lowering effect was assumed to involve the adrenergic action of the compound. According to the present state of the art, adrenergic activity is believed to reside almost exclusively in the $l$-isomer of adrenergic phenethanolamines such as adrenalin, isoproterenol, soterenol, salbutamol, carbuterol, terbutaline, and metaproterenol.

It has now been discovered that topical administration of the pure dextrorotatory stereoisomer of isoproterenol and other beta-adrenergic stimulants to the mammalian eye effectively lowers intraocular pressure in a dose-related fashion without the intrusion of any significant adrenergically mediated side effects on pupil size, heart rate and blood pressure resulting from drug absorption. For instance, ocular instillation of an effective intraocular lowering dose of the $d$-stereoisomer of isoproterenol does not produce any significant increase in heart rate compared to an equimolar dose of $dl$-isoproterenol which results in at least a 50% increase in heart rate.

The present invention is based on the highly unexpected finding that ocular instillation of "so-called pharmacologically inactive" $d$-stereoisomers of phenethanolamine beta-adrenergic stimulating agents effectively lower intraocular pressure in the mammal. This is an extremely significant and important discovery since, heretofore, $d$-stereoisomers of beta-adrenergic stimulators such as isoproterenol, soterenol, salbutamol, carbuterol, terbutaline, metaproterenol, and the like were found to be many orders of magnitude pharmacologically less active (to the point of being without practical utility) than the $l$-stereoisomer or racemate; refer to Lands, et al., J. Pharm. Exptl. Therap., 111, 469–474 (1954); D. Colella, et al., The Pharmacologist, 15 (No. 2) 464 (1973).

In accord with the present invention, a substituted $d$-phenethanolamine characterized by Formula I or an ophthalmologically acceptable salt thereof applied topically to the eye in an effective ophthalmologically acceptable amount provides a therapeutically useful reduction in intraocular pressure which has a duration of from 4 to 6 hours. It is to be understood that the term "effective ophthalmologically acceptable amount" as used herein refers to the quantity of active ingredient necessary to lower intraocular pressure without causing any harmful or deleterious side effects associated with adrenergic activation such as tachycardia, mydriasis, hypertension and hypotension. The process of the present invention comprises topical administration of a composition consisting of a compound of Formula I or an ophthalmologically acceptable salt thereof containing from 0.16% to 5.2% by weight of the base form of said compound in an amount sufficient to deliver an effective dose of from 0.08 mg. to 10.4 mg. per eye and a non-toxic pharmaceutically acceptable ophthalmological carrier therefor. Compounds of Formula I particularly preferred for their intraocular lowering effect and absence of adrenergically mediated side effects such as tachycardia are selected from the group consisting of the dextrorotatory stereoisomers of isoproterenol, soterenol, salbutamol, carbuterol, terbutaline and metaproterenol. These compounds are identified below according to structural formula.

TABLE I

STRUCTURAL FORMULAS OF PREFERRED INTRAOCULAR LOWERING COMPOUNDS

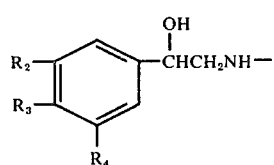

Formula I

| Name | $R_1$ | $R_2$ | $R_3$ | $R_4$ |
|---|---|---|---|---|
| Isoproterenol | $CH(CH_3)_2$ | OH | OH | H |
| Soterenol | $CH(CH_3)_2$ | $CH_3SO_2NH$ | OH | H |
| Salbutamol | $CH(CH_3)_2$ | $HOCH_2$ | OH | H |
| Carbuterol | $C(CH_3)_3$ | $\underset{NH_2CNH}{\overset{O}{\parallel}}$ | OH | H |
| Terbutaline | $C(CH_3)_3$ | OH | H | OH |
| Metaproterenol | $CH(CH_3)_2$ | OH | H | OH |

A group of compounds of Formula I preferred for their high degree of intraocular lowering activity and absence of tachycardia compared to the $dl$-racemate consists of $d$-isoproterenol, $d$-soterenol, and $d$-salbutamol. $d$-Isoproterenol is a particularly preferred compound.

Aspects of this invention include an ophthalmologic process for reducing intraocular pressure by topical administration of $d$-phenethanolamines of Formula I, compositions adapted for practicing it, and methods of administration by polymeric insert or soft contact lens.

When compounds of Formula I are administered topically to the mammalian eye, a solution having a concentration in the range of 0.16% to 5.2% by weight and preferably 0.16% to 3.4% by weight, the latter in an aqueous isotonic vehicle such as 0.9% sodium chloride, is preferred. One to four drops of such solution is sufficient. Other vehicles and additional active ingredients may be included in the compositions. The foregoing concentration ranges were selected on the basis of measurements made in rabbits treated according to the present invention. The literature on the subject indicates that precedence exists for believing that the same concentration ranges will be preferred for man and other species also, but some species variation and sensitivity may be encountered.

In the case of isoproterenol, the most preferred concentration range is from 0.65% to 2.6% by weight since the maximal intraocular pressure lowering effect is achieved within this range. Solutions having a concentration greater than 2.6% by weight may be employed, but no added benefit with respect to reducing intraocular pressure above that concentration is generally obtained. However, solutions of $d$-isoproterenol having concentrations of up to 10.2% by weight have been administered without ill effect. At concentrations of less than 0.6% by weight, only a minimal intraocular lowering effect is obtained.

In practicing the process of the present invention, it is essential that the $d$-stereoisomers of Formula I be substantially free of the $l$-stereoisomer otherwise there is a decrease in activity and an increase in beta-adrenergically mediated side effects such as heart rate. The d-stereoisomers of Formula I are preferably used in the form of an ophthalmologically acceptable water soluble salt such as tartrate, bitartrate, sulfate, or hydrochloride. The weight concentrations of the solutions employed in the process of the present invention are expressed herein in terms of the base forms of Formula I and, in practicing the invention, a water soluble ophthalmologically acceptable salt is generally selected for use and administered in an amount sufficient to provide the concentrations referred to above.

The dl-racemic forms of the compounds of Formula I are well known beta-adrenergic stimulating agents prepared from the appropriate aryl methyl ketone according to methods elaborated by R. T. Brittain, et al., Advances in Drug Research, Vol. 5, page 209 (1970). Resolution of the racemic forms by conventional methods such as salt formation with an optically active acid followed by fractional crystallization affords the optically active d-stereoisomers of phenethanolamines characterized by Formula I.

DESCRIPTION OF SPECIFIC EMBODIMENTS

I. Treatment Process

A so-called water provocative test is used clinically in man to aid in the diagnosis of primary open angle glaucoma. According to the diagnostic procedure the patient is required to drink a pre-determined quantity of water and the intraocular pressure is measured at intervals thereafter. This procedure has been adapted to the evaluation of chemical entities possessing anti-glaucoma activity in rabbits by McDonald, et al. loc. cit. and validated with respect to various drugs which are effective for lowering intraocular pressure in man including epinephrine bitartrate, l-isoproterenol bitartrate, pilocarpine hydrochloride, physostigmine salicylate, etc. It has been adapted as follows for demonstrating the operativeness of the present invention.

Female New Zealand white rabbits weighing from 1.8 to 2.5 kg. each were grossly examined for ocular defects that might preclude their use in the test. Each rabbit was kept unanesthetized in a restrainer box throughout the experiment. Food was withheld for approximately 18 hours prior to the use of the animals in the experiment. Intraocular pressures were measured with a Mackay-Marg Model No. 12 electronic tonometer (Biotronics, Inc., 838 Butte Street, Redding, Calif., 96001; E. Marg, Journal of the American Optometric Association, 34, 961–5 (1963)).

Intraocular pressure was measured at the outset to obtain a normal value and then the rabbits were given tap water, approximately 60 ml./kg. of body weight rapidly via gavage. Intraocular pressures were again measured 10, 20 and 30 minutes later to determine the peak increase in intraocular pressure resulting from the water loading. The procedure was then repeated in the same animals, 2, 4, and 6 hours later following topical application of the test drug or control solutions. In each instance, after water load, there is a substantial increase in intraocular pressure (unless controlled by the test drug) which reaches maximal elevation within 30 minutes and returns to pretreatment levels before the next water load.

Drug solutions were prepared by dissolving the test agent in 0.9% aqueous saline vehicle. In the test procedure, 100 $\mu$l. (approximately two drops) of the test solution was applied to one eye and 0.9% saline was applied to the contralateral eye which serves as the control eye during the course of the experiment. Pretreatment measurements (designated 0-hours) were previously made of normal intraocular pressure, and of the response to water loading to establish that no significant difference in intraocular pressure between the test eye and the contralateral control eye existed prior to the administration of the solution of the test agent. Test solutions were randomized between right and left eyes. By comparing the change (reduction) in intraocular pressure in the test eye compared to the contralateral eye, which serves as a control, a measure of the effectiveness of the test agent as an intraocular lowering agent is obtained. The diameter of the pupil was measured under constant illumination to the nearest 0.5 millimeter with a clear straight edge ruler. Blood pressure and heart rate were measured in unanesthetized rabbits with a force displacement transducer via cannulation of the central artery of the xylocaine infiltrated ear. Separate groups of animals were used for the cardiovascular and intraocular pressure experiments.

The effectiveness of representative phenethanolamines of Formula I in the process of the present invention as measured by the above test procedure can be seen by comparative data presented in Table II.

TABLE II

Comparative Effects of Equimolar Amounts of the d and dl Forms of Isoproterenol, Soterenol and Salbutamol on Intraocular Pressure, Heart Rate and Pupil Size Two Hours After Topical Application to Eyes of Unanesthetized Rabbits

| Drug | Conc. Tested[1] (%) | No. Animals | Intraocular Pressure[2] (Mean ± S.E.) | | | | | |
|---|---|---|---|---|---|---|---|---|
| | | | Pretreatment mm hg | | Post-Treatment[3] mm Hg | | Reduction[4] | |
| | | | Drug Eyes | Saline Eyes | Drug Eyes | Saline Eyes | mm Hg | % |
| dl-Isoproterenol HCl | 3.0 | 6 | 29.8 ± 2.0 | 31.2 ± 2.0 | 25.7 ± 1.6 | 30.2 ± 2.0 | 4.5 ± 1.3 | 14.4 ± 3.7 |
| d-Isoproterenol bitartrate | 4.4 | 6 | 29.5 ± 1.0 | 29.3 ± 0.9 | 23.0 ± 1.2 | 32.8 ± 2.2 | 9.8 ± 1.3 | 29.3 ± 3.0 |
| dl-Soterenol HCl | 3.9 | 7 | 31.7 ± 0.9 | 30.8 ± 1.1 | 25.9 ± 1.0 | 31.7 ± 1.4 | 5.9 ± 1.3 | 17.8 ± 3.9 |
| d-Soterenol HCl | 3.9 | 7 | 30.6 ± 1.1 | 30.6 ± 0.9 | 21.9 ± 1.0 | 30.9 ± 1.1 | 9.0 ± 0.7 | 29.2 ± 1.9 |
| dl-Salbutamol Base | 2.8 | 6 | 26.8 ± 1.3 | 27.2 ± 0.8 | 23.7 ± 1.1 | 24.5 ± 1.2 | 0.8 ± 0.8 | 4.5 ± 2.5 |
| dl-Salbutamol SO₄ | 3.4 | — | — | — | — | — | — | — |
| d-Salbutamol Acetate Monomethanolate | 4.0 | 6 | 31.7 ± 1.1 | 32.2 ± 1.9 | 26.2 ± 1.4 | 33.3 ± 1.5 | 7.2 ± 2.0 | 20.7 ± 5.2 |

TABLE II-continued

Comparative Effects of Equimolar Amounts of the d and dl Forms of Isoproterenol, Soterenol and Salbutamol on Intraocular Pressure, Heart Rate and Pupil Size Two Hours After Topical Application to Eyes of Unanesthetized Rabbits

| Drug | Conc. Tested[1] (%) | No. Animals | Heart Rate (Mean ± S.E.) | | | | Effect on Pupil Size |
|---|---|---|---|---|---|---|---|
| | | | Pretreatment Beats/min | Post-Treatment[5] | | | |
| | | | | Beats/min | Increase[6] | | |
| | | | | | Beats/min | % | |
| Saline | 0.9 | — | — | — | — | — | — |
| dl-Isoproterenol HCl | 3.0 | 4 | 233.0 ± 24.8 | 371.8 ± 10.1 | 138.8 ± 20.9 | 65.6 ± 19.2 | None |
| d-Isoproterenol bitartrate | 4.4 | 5 | 233.0 ± 12.3 | 266.0 ± 12.1 | 32.0 ± 5.1 | 13.9 ± 2.6 | None |
| dl-Soterenol HCl | 3.9 | 6 | 229.1 ± 9.1 | 275.8 ± 8.2 | 46.7 ± 13.3 | 21.5 ± 6.8 | Mydriasis |
| d-Soterenol HCl | 3.9 | 3 | 233.3 ± 8.8 | 250.0 ± 10.0 | 16.7 ± 3.3 | 7.1 ± 1.5 | None |
| dl-Salbutamol Base | 2.8 | — | — | — | — | — | None |
| dl-Salbutamol SO$_4$ | 3.4 | 4 | 217.5 ± 14.9 | 285.0 ± 5.0 | 67.5 ± 18.4 | 33.1 ± 10.2 | — |
| d-Salbutamol Acetate Monomethanolate | 4.0 | 3 | 211.7 ± 22.4 | 231.7 ± 22.0 | 20.0 ± 10.0 | 9.8 ± 5.1 | None |
| Saline | 0.9 | 8 | 216.5 ± 11.5 | 243.1 ± 11.2 | 27.9 ± 7.9 | 14.0 ± 4.5 | — |

In the above table, the numerical superscripts 1–6 refer to the footnotes below:
1. Drug concentrations are equimolar with respect to base.
2. Water load induced elevated intraocular pressure in rabbits.
3. Two hours after topical drug application to the eye.
4. Reduction of intraocular pressure in drug-treated as compared to contralateral, saline-treated eyes.
5. Maximum occurring within 60 minute interval after topical drug application to the eye.
6. Post-treatment as compared to pretreatment heart rate.

Pretreatment values listed in the above table for intraocular pressure with respect to the drug eye and saline eye establish that no initial significant difference exist prior to the administration of the test drug and therefore reduction in intraocular pressure is a valid measure of the effectiveness of the test agent.

The increase in heart rate seen for the "d-stereoisomers" is not significant inasmuch as the saline solution which serves as a vehicle for administering the test agent produces a 14% increase in heart rate.

As is evident from the data, intraocular pressure measurements before and after topical administration of d-isoproterenol, d-soterenol, and d-salbutamol conclusively show that d-stereoisomers are substantially more effective in lowering intraocular pressure than the corresponding dl-forms. Activity ratios (d-/dl-) for isoproterenol, soterenol, and salbutamol are 2.2, 1.6 and 4.6 respectively. This increased efficacy is obtaned without inducing adverse side effects such as tachycardia or mydriasis. The reduction in intraocular pressure by the dextrorotatory phenethanolamines of Formula I is outstanding when considered in the light of prior art which teaches that, with respect to biological action, the d-stereoisomers of beta-adrenergic phenethanolamines such as isoproterenol, soterenol, and salbutamol have minimal activity and are generally considered pharmacologically ineffective as adrenergic agents.

II. Compositions

Pharmaceutical composition comprised of a compound of Formula I and a non-toxic pharmaceutically acceptable ophthalmological carrier therefor which are suitable for ocular instillation are preferred for practice of the present invention. These include ophthalmic solutions and ointments. Aqueous ophthalmic solutions formulated in accord with good pharmaceutical practice as set forth for instance in Chapter 83 of Remington's Pharmaceutical Sciences, 14th Edition, Mack Publishing Company are preferred, although petrolatum based ointments may be employed. The ophthalmic solutions are sterile and preferably contain a bacteriological preservative to maintain sterility during use. The quaternary ammonium bacteriostats such as benzalkonium chloride are satisfactory. An antioxidant is also used in those cases wherein the phenethanolamines of Formula I such as d-isoproterenol are highly susceptible to oxidative decomposition. Suitable antioxidants include sodium bisulfite, N-acetylcysteine salts, sodium ascorbate and other water soluble ophthalmologically acceptable antioxidants known to the pharmaceutical art.

Tonicity of the solution of the Formula I compounds is adjusted with inert ingredients such as sodium chloride or boric acid to provide a solution which is comfortable for application to the eye. For example, compositions containing up to about 4.4% d-isoproterenol bitartrate or 3.0% hydrochloride, 0.9% sodium chloride, or a vehicle of equivalent tonicity such as 1.9% boric acid may be employed. For higher concentrations of d-isoproterenol salts, water alone or a sodium chloride solution of less than 0.9% concentration or other vehicle of appropriate tonicity may be employed.

Ointments are prepared with conventional petrolatum vehicles employing liquid petrolatum and white petrolatum in such proportions as to afford an ointment of desirable fluidity.

Ophthalmic Solution

| | |
|---|---|
| d-Isoproterenol | 4.40 g. |
| Benzalkonium chloride | 0.01 g. |
| Sodium bisulfite | 0.10 g. |
| Water, q.s. | 100.00 g. |

If desired, 0.9% by weight aqueous sodium chloride may replace water as the solvent. The solution is sterilized by filtration and asceptically packaged. d-Isoproterenol tartrate, d-isoproterenol sulfate, or d-isoproterenol hydrochloride may be substituted for d-isoproterenol bitartrate in chemically equivalent (equimolar) amounts.

Ophthalmic Ointment

| | |
|---|---|
| d-Isoproterenol bitartrate, micronized | 1.1 g. |
| White petrolatum, q.s., Liquid petrolatum, q.s., | 100.0 g. |

The product is prepared and packaged under asceptic conditions to yield a sterile ointment.

By substituting an equimolar amount of the compounds of Formula I, (e.g., d-soterenol, d-salbutamol, d-carbuterol, d-terbutaline, d-metaproterenol) or Formula II for d-isoproterenol in the foregoing formulations, additional ophthalmic ointments and solutions are provided.

The phenethanolamines of Formula I such as d-isoproterenol and piperidylcarbinols of Formula II, and ophthalmologically acceptable acid addition salts thereof, may also be applied to the eye through the vehicle of a polymeric insert or soft contact lens. For the latter purpose the polymeric hydrophilic hydrogels prepared from polymers of acrylic and methacrylic esters, modified collagens, cross-linked polyether gels, cross-linked polyvinyl alcohol, or cross-linked partially hydrolyzed polyvinylacetate as disclosed in U.S. Pat. Nos. 2,976,576, 3,220,960, and 3,419,006 may be employed. Ocular inserts prepared from these or other polymeric materials which are insoluble in tear liquid but which may absorb tear liquid to form a swollen hydrogel as disclosed in U.S. Pat. Nos. 3,416,530, 3,618,604, may also be employed. All such means of applying d-isoproterenol or an ophthalmologically acceptable salt thereof or other compounds of Formula I to the eye are included within the present invention as are compositions adapted for such use.

In practicing the process of the present invention for lowering intraocular pressure by topical administration of compounds of Formula I and Formula II, an ophthalmologically acceptable polymeric ocular insert placed and retained in contact with an eyeball is preferred wherein the compound diffuses from the insert at a rate sufficient to provide an effective intraocular pressure lowering dose from 0.08 mg. to 10.4 mg. over a period of 6 hours.

Ocular inserts particularly preferred in the practice of the process of the present invention are conventionally prepared, for example, by soaking the polymeric insert or soft lens in a 0.16% to 5.2% solution of a Formula I or II compound or an ophthalmological salt thereof until equilibrium is established, which is generally within a period of 1 to 5 minutes. Inserts prepared in this manner diffuse at a rate sufficient to provide a dose of from 0.08 mg. to 10.4 mg. to the eyeball over a period of 6 hours.

The process of the present invention concerned with lowering intraocular pressure in the mammalian eye comprising topical application thereto an effective ophthalmologically acceptable amount of the dextrorotatory stereoisomer of compounds of Formula I or an ophthalmologically acceptable acid addition salt thereof also includes topical administration of a compound or an ophthalmologically acceptable acid addition salt thereof selected from the group of piperidylcarbinols characterized by Formula II

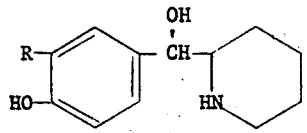

Formula II wherein R is hydroxy, hydroxymethyl or methanesulfonamido.

Specific compounds of Formula II preferred for their high degree of intraocular lowering activity and absence of adrenergically mediated side effects are identified below:

| A | Name |
|---|---|
| $CH_3SO_2NH$ | d-4-Hydroxy-3-methanesulfonamidophenyl-2-piperidylcarbinol |
| $CH_2OH$ | d-4-Hydroxy-3-hydroxymethylphenyl-2-piperidylcarbinol |
| OH | d-3,4-Dihydroxyphenyl-2-piperidylcarbinol. |

It is to be understood that method of administration, pharmaceutical compositions, percent concentrations and dosage ranges set forth hereinabove in the instant process for compounds of Formula I are applicable to compounds of Formula II and ophthalmologically acceptable salts thereof. The dextrorotatory stereoisomer of both erythro and threo-diastereoisomeric forms of the compounds of Formula II are useful in the instant process with the d-stereoisomer of the erythro diastereoisomer particularly preferred.

U.S. Pat. No. 3,743,737 discloses preparation of erythro and threo 4-hydroxy-3-methanesulfonamidophenyl-2-piperidylcarbinol and that the erythro and threo-stereoisomers may be resolved to provide the d-optical isomers. U.S. Pat. No. 3,655,676 discloses preparation of 4-hydroxy-3-hydroxymethylphenyl-2-piperidylcarbinol and separation of the erythro and threo-diastereoisomers by fractional crystallization. I Carney, et al., Arch. Int. Pharmacodyn., 194, 334–345 (1971) discloses 3,4-dihydroxyphenyl-2-piperidylcarbinol.

The dextrorotatory forms of the compounds of Formula II are obtained by resolving the racemic erythro and threo-stereoisomers in accordance with the procedures well-known to the art as illustrated herein for the d-stereoisomers of Formula I.

What is claimed is:

1. The process of lowering intraocular pressure in the eye of a mammal suffering from primary open angle glaucoma which comprises topical application thereto of an effective ophthalmologically acceptable amount for lowering intraocular pressure of the dextrorotatory stereoisomer substantially free of the levorotatory stereoisomer of a compound selected from the group consisting of a phenethanolamine having Formula I

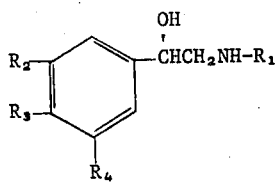

Formula I wherein
R₁ is isopropyl or tert.-butyl;
R₂ is methanesulfonamido; and one of
R₃ and R₄ is hydrogen and the other is hydroxy; and an ophthalmologically acceptable acid addition salt thereof said amount being substantially free of adrenergically mediated side effects.

2. The process of claim 1 wherein the ophthalmologically acceptable salt is water soluble and is applied topically in an aqueous solution.

3. The process of claim 2 wherein said solution contains a molar amount of said water soluble ophthalmologically acceptable salt of said phenethanolamine equivalent to from 0.16 to 5.2% by weight of said phenethanolamine.

4. The process of claim 1 wherein said compound is topically applied by an ophthalmologically acceptable polymeric ocular insert placed and retained in contact with the eyeball, said compound being diffusible from said insert at a rate sufficient to provide an ophthalmologically acceptable effective intraocular pressure lowering dose thereof to the eyeball when said insert is in contact therewith.

5. The process of claim 4 wherein an effective intraocular pressure lowering dose of said compound of from 0.08 mg. to 10.4 mg. is delivered to the eyeball over a period of 6 hours.

6. The process of claim 1 wherein said compound is d-soterenol.

7. The process of claim 1 wherein said compound is d-soterenol hydrochloride.

* * * * *